(12) United States Patent  (10) Patent No.: US 6,524,328 B2
Levinson  (45) Date of Patent: Feb. 25, 2003

(54) SUTURE LOCK, LOCK APPLICATOR AND METHOD THEREFOR

(75) Inventor: Melvin E. Levinson, Miami, FL (US)

(73) Assignee: Scion International, Inc., Miami, FL (US)

( * ) Notice: Subject to any disclaimer, the term of this patent is extended or adjusted under 35 U.S.C. 154(b) by 0 days.

(21) Appl. No.: 09/833,910

(22) Filed: Apr. 12, 2001

(65) Prior Publication Data

US 2002/0188321 A1 Dec. 12, 2002

(51) Int. Cl.$^7$ ............................................... A61B 17/04
(52) U.S. Cl. ........................ 606/232; 606/139; 606/151
(58) Field of Search ............................... 606/232, 139, 606/151; 24/115 R, 115 M

(56) References Cited

U.S. PATENT DOCUMENTS

| | | | | |
|---|---|---|---|---|
| 4,750,492 A | * | 6/1988 | Jacobs | 606/230 |
| 5,368,599 A | | 11/1994 | Hirsch et al. | 606/139 |
| 5,514,159 A | * | 5/1996 | Matula et al. | 24/115 H |
| 5,669,917 A | * | 9/1997 | Sauer et al. | 606/139 |
| 5,899,921 A | * | 5/1999 | Caspari et al. | 606/151 |
| 6,086,608 A | * | 7/2000 | Ek et al. | 606/232 |
| 6,099,553 A | * | 8/2000 | Hart et al. | 24/115 A |
| 6,126,677 A | * | 10/2000 | Ganaja et al. | 606/232 |
| 6,165,204 A | * | 12/2000 | Levinson et al. | 606/151 |
| 6,200,329 B1 | * | 3/2001 | Fung et al. | 606/232 |
| 6,231,592 B1 | * | 5/2001 | Bonutti et al. | 606/148 |
| 6,290,711 B1 | * | 9/2001 | Caspari et al. | 606/232 |

* cited by examiner

Primary Examiner—Rodney M. Lindsey
(74) Attorney, Agent, or Firm—Robert C. Kain, Jr.; Fleit Kain

(57) ABSTRACT

The suture lock or suture lock rivet for locking suture thread includes a lock head defining a cut-out, a first locking surface and a stem connected via a breakaway section. The lock also includes a lock base defining a second complementary locking surface. The locking surfaces trap the suture in the cut-out. The stem breaks away. A suture lock applicator is utilized to deliver and apply the suture lock to the surgical site. The system includes the lock loaded within the suture lock applicator. The applicator, or rivet gun, is designed to grip the stem body and coact with the lock base to cause the lock base to slide over the stem towards the lock head or rivet head, and subsequently, with the application of additional longitudinally directed force, to remove the stem from the lock head or first body part at the breakaway section.

22 Claims, 4 Drawing Sheets

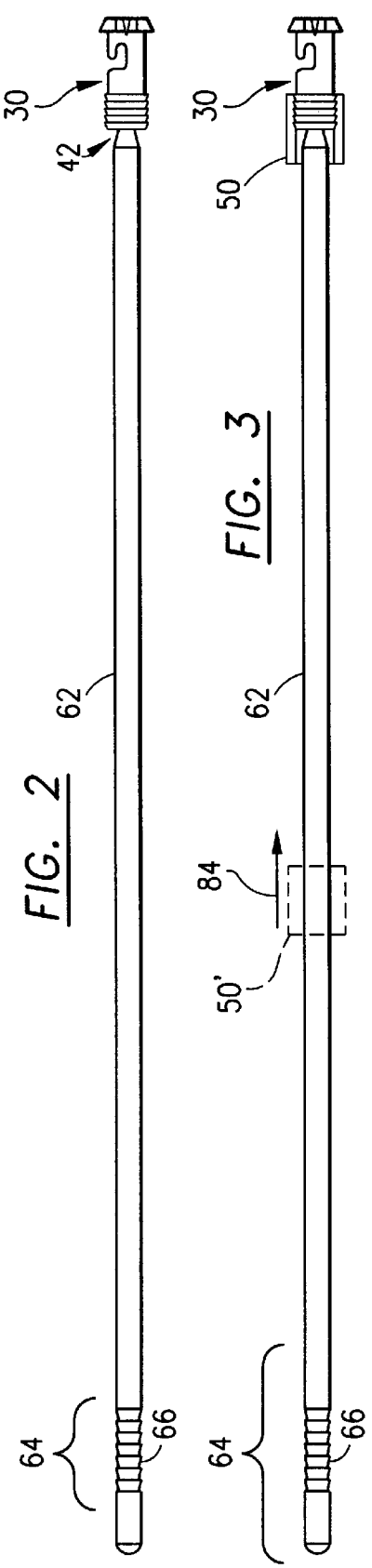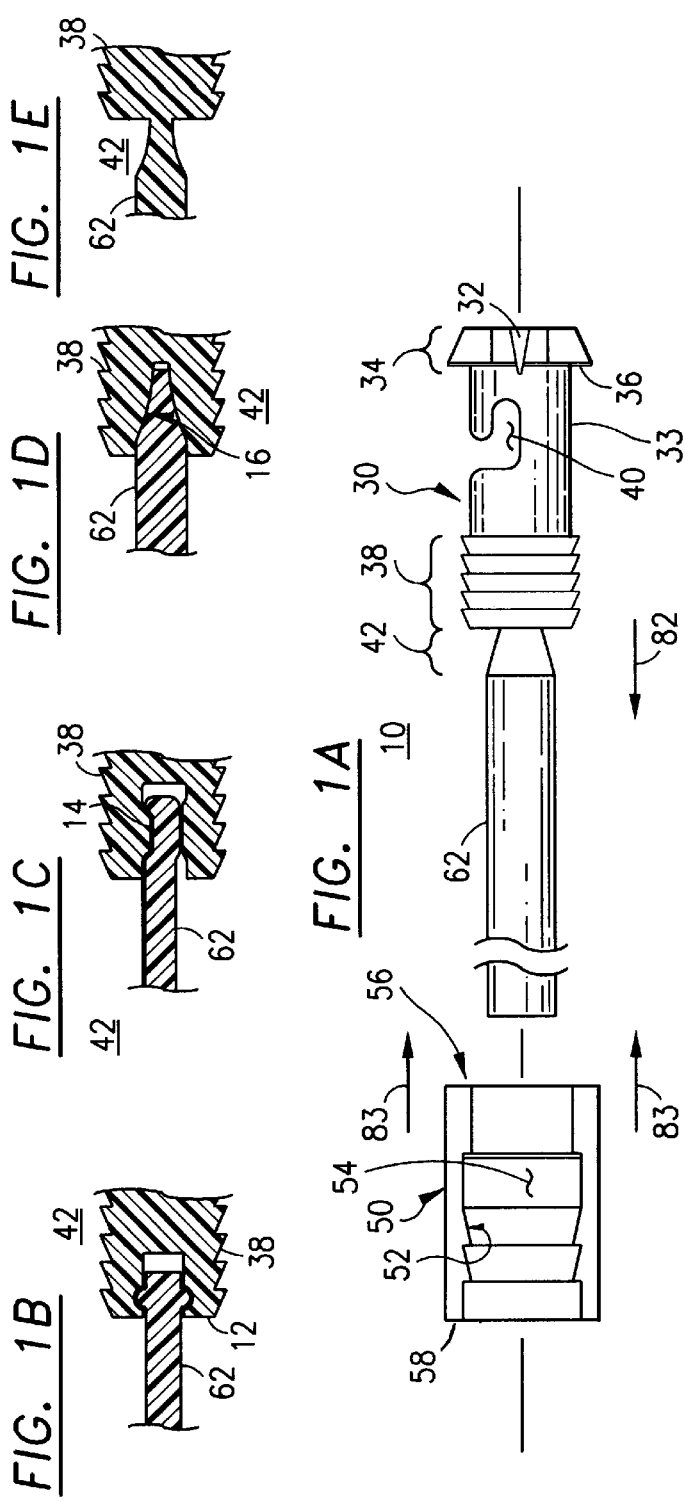

FIG. 6
FIG. 7
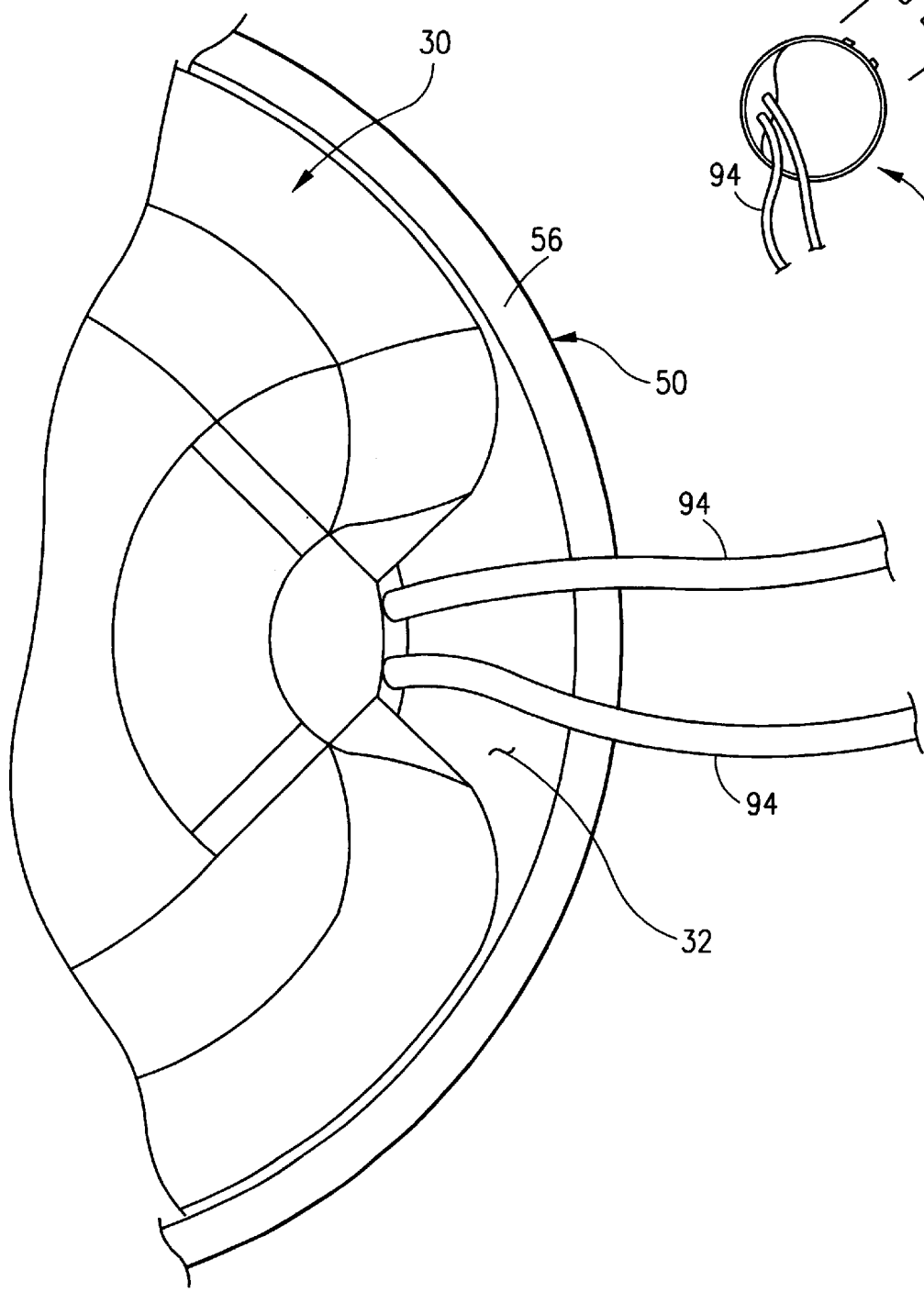
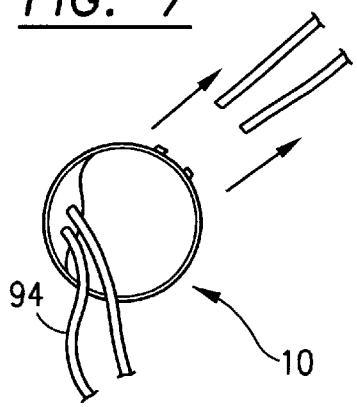

SUTURE LOCK, LOCK APPLICATOR AND METHOD THEREFOR

The present invention relates to a suture lock or suture lock rivet utilized to lock suture threads previously positioned at a surgical site. The suture lock or suture lock rivet and an associated suture lock applicator and rivet gun are designed to be inserted into a small size access port on a cannula. The present invention also relates to a method for locking suture threads drawn tight at a surgical site.

BACKGROUND OF THE INVENTION

The current trend in minimally invasive surgery is to utilize smaller and smaller cannula (ports of access) to gain access to the surgical site. Currently, 5 mm ports are being used instead of the traditional 10 mm port for instrument access. Some access cannula are being utilized with a 2 or 3 mm orifice. Consequently, new instruments and new designs are required for surgical techniques accomplished through such restricted spaces.

During minimally invasive surgery, one of the tasks commonly involved is the suturing of the organ or body part being operated on. Because the cannula is so small, simple tasks such as suturing become difficult to accomplish using traditional methods. The present invention solves the problem of closing or "tying off" previously inserted suture threads.

OBJECTS OF THE INVENTION

It is an object of the present invention to provide a specially designed suture lock or suture lock rivet capable of being utilized in minimally invasive surgery.

It is an object of the present invention to provide a specially designed suture lock or suture lock rivet utilized to "tie off" or lock suture threads previously inserted at a surgical site.

It is another object of the present invention to provide a system including a suture lock applicator capable of delivering a suture lock to a surgical site and capable of manipulating the suture lock such that it captures both sides of a single suture thread or the extending ends of multiple embedded suture threads in order to draw the suture threads tight, thus closing the surgical site, and then locking the drawn suture threads within the suture lock.

It is yet another object of the present invention to provide a system including a suture lock rivet gun capable of delivering a suture lock rivet to a surgical site and capable of manipulating the suture lock rivet such that it captures both sides of a single suture thread or the extending ends of multiple embedded suture threads in order to draw the suture threads tight, thus closing the surgical site, and then locking the drawn suture threads within the suture lock rivet.

It is another object of the present invention to provide a method for locking previously placed suture threads.

SUMMARY OF THE INVENTION

The suture lock utilized for locking at least one suture thread includes an elongated lock head defining a cut-out adapted to capture the suture thread therein, the locking head also defining a first locking surface thereon and having a stem connected via a breakaway section to the locking head. The suture lock also includes a lock base defining a longitudinal passage adapted to mate with the elongated lock head. The lock base also defines a second locking surface complementary to the first locking surface on the lock head. The two locking surfaces are adapted to lock the lock base onto the lock head such that the suture thread is trapped in the cut-out by the base. The stem is adapted to break away from the lock head at the breakaway section. The lock head and lock base may also include respective intersecting edges adapted to cut a suture thread placed therebetween. The suture lock may be envisaged as a suture lock rivet including a rivet head and a two-part rivet stem. The first body part of the stem defining a cut-out adapted to capture the suture thread therein, and the second body part connected to the first body part via a breakaway section. The suture lock rivet also includes a lock base similar to the lock base of the suture lock. The suture lock rivet functions similar to the suture lock. A suture lock applicator is utilized to deliver and apply the suture lock or suture lock rivet to the surgical site. The system of the suture lock and suture lock applicator includes the suture lock loaded within the suture lock applicator. The suture lock applicator includes a stationary handle member and an elongated applicator tube attached thereto, the applicator tube having an end face adapted to abut the aforementioned lock base. The suture lock applicator also includes a movable handle member movably coupled to the applicator tube such that the movable handle member and the stationary handle member cooperate together. The movable handle member includes an actuator tooth which cooperates with a peripheral lock face on the aforementioned stem such that movement of the movable handle member causes the actuator tooth to engage the peripheral lock face which causes longitudinal movement of the stem with respect to the applicator tube. The movement causes the lock base to lock onto the lock head. Further excessive longitudinal movement causes the stem to detach from the lock head at the breakaway section.

BRIEF DESCRIPTION OF THE DRAWINGS

Further objects and advantages of the present invention can be found in the detailed description of the preferred embodiments when taken in conjunction with the accompanying drawings in which:

FIG. 1A conceptually illustrates a suture lock or suture lock rivet prior to application at a surgical site;

FIGS. 1B, 1C, 1D and 1E diagrammatically illustrate cross-sectional views of possible connections between a lock head or rivet and a corresponding stem;

FIG. 2 diagrammatically illustrates a lock head or rivet head with a connected elongated stem or rivet stem;

FIG. 3 diagrammatically illustrates a lock base partially fastened to the lock head or rivet stem;

FIG. 6 diagrammatically illustrates a top view of the suture lock head or rivet head with two suture threads captured thereat; and FIG. 7 diagrammatically illustrates the suture lock or suture lock rivet with the excess suture thread having been cut by the suture lock or suture lock rivet.

DETAILED DESCRIPTION OF THE PREFERRED EMBODIMENTS

Figure 4:
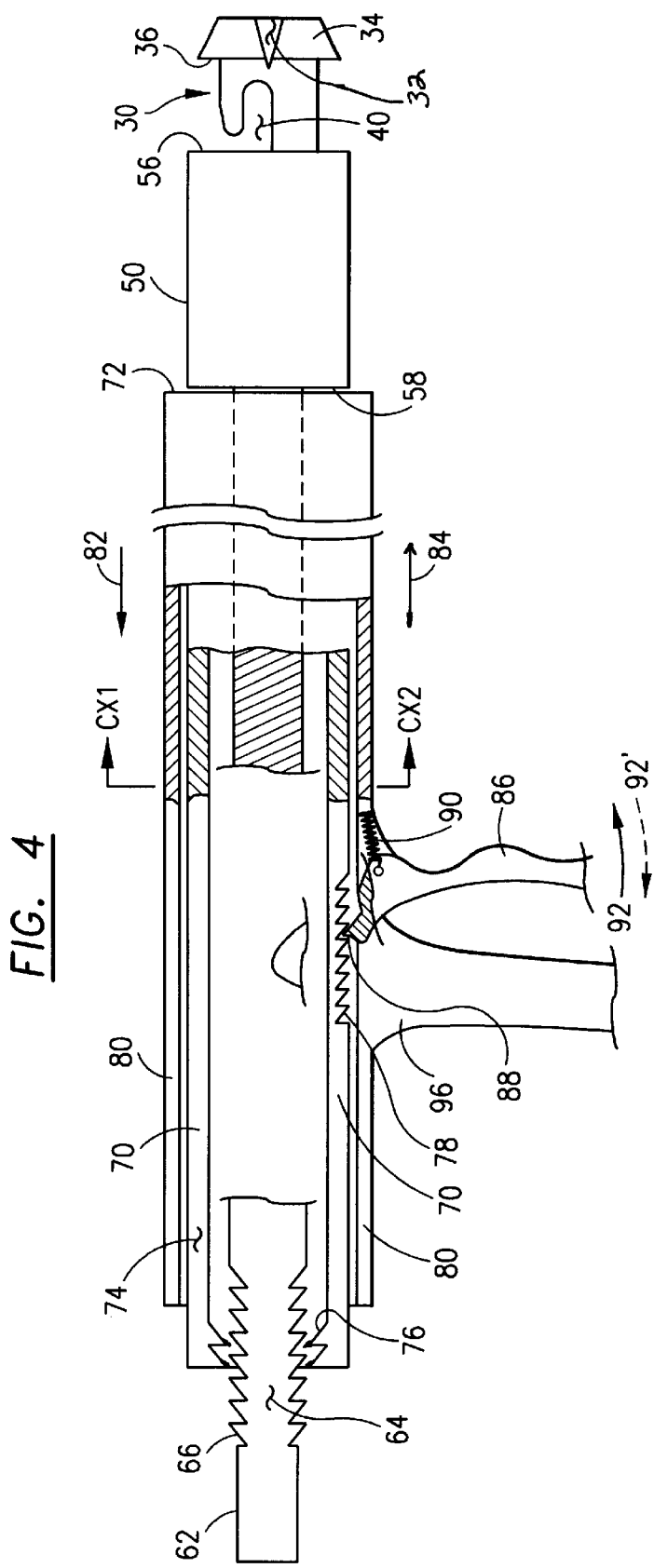
FIG. 4 diagrammatically illustrates a suture lock applicator with a suture lock or suture lock rivet loaded in the applicator.

The present invention relates to a suture lock or suture lock rivet utilized to lock suture threads previously positioned at a surgical site, an applicator for delivery and utilization of the suture lock or suture lock rivet, and a method for locking suture threads at remote, minimally accessible surgical sites. The suture lock or suture lock rivet and applicator disclosed herein may be used to lock a single suture thread having either end of the suture thread embedded into a bodily structure, or may be used to lock more than one suture thread, each suture thread having been previously positioned at the surgical site.

For ease in understanding the present invention, the term "distal" shall refer to a direction or location near the surgical site and away from the physician or healthcare technician, and the term "proximal" shall refer to a direction or location closer to the physician or healthcare technician. Similar features are represented by the same reference number throughout the drawings.

FIG. 1A conceptually illustrates a suture lock or suture lock rivet 10. Suture lock 10 includes elongated lock head 30 and lock base 50. In FIG. 1A, lock head 30 is connected to the distal end of elongated stem 62 via breakaway section 42. Stem 62 is utilized in the delivery and application of suture lock 10. Stem 62 is detachably coupled to head 30 such that it breaks away from head 30 when sufficient pulling force is applied along the longitudinal axis of stem 62 in the direction 82. The connection between stem 62 and head 30 may be formed through a weak link between the two, as depicted in FIGS. 1A, 1E, 2 and 3 or may be a detent coupling 12 (FIG. 1B), a latch 14 (FIG. 1C), or a friction lock 16 (FIG. 1D), established between the abutting surfaces of the two structures.

The distal end of head 30 includes a v-shaped cut-out, channel, cavity or groove 32 defined lengthwise along part of the head's longitudinal axis. Head 30 in FIGS. 1, 2 and 3 includes a distal disc-shaped end piece or end cap 34 having beveled edges. Cap 34 may have other shapes but should be radially or peripherally larger than the body of head 30. Cut-out 32 traverses end cap 34. Cut-out 32 in the working embodiment is wide enough, typically 0.03 inches, to accommodate at least the thickness of a suture thread therein. End cap 34 includes a proximally facing surface 36. Surface 36 can include a sharp edge utilized to cut a suture thread pressed against it. Surface edge face 36 ends at either side of cut-out 32 such that a suture thread placed in cut-out 32 is unaffected by the cutting properties of the edge.

Cut-out 32 may also include a cavity 40, located proximal of the distal end of head 30. Cavity 40 should be large enough to accommodate at least one suture thread therein. Cavity 40 is aligned such that if a suture thread were placed within cavity 40 it would extend outboard of cavity 40 and into cut-out 32, i.e., the suture thread would extend proximally through cut-out 32 and into cavity 40. Typically, cavity 40 is shaped such that a suture thread placed therein is trapped during fastening of suture lock 10. Head 30 also includes aproximally located, locking surface 38. In this specification, locking surface 38 will be referred to as first locking surface 38. First lock surface 38 may he one continuously curved smooth surface, or include multiple ridges, as illustrated in FIGS. 1A, 2 and 3. First locking surface 38 is designed to interface with a corresponding, complementary second locking surface 52 defined within base 50.

Lock base 50 cooperates with lock head 30 to trap and lock suture threads thereat. Base 50 defines a longitudinal passage 54 through which passes stem 62 and which is adapted to mate with the elongated, proximal end segment of lock bead 30. Although illustrated as cylindrical in the drawings, both head 30 and base 50 may define other shapes, including rectangular or any other polygonal structure. The interlocking and mating action by base 50 onto head 30, or alternatively, head 30 into base 50, is important Base 50 includes a second locking surface 52. Second locking surface 52 may be one continuously curved smooth surface, or include multiple ridges, as illustrated in FIGS. 1A and 3. As previously described, second locking surface 52 and first locking surface 38 are complementary and are adapted to lock base 50 onto head 30. These surfaces define saw teeth in a preferred embodiment. The purpose of the ridges on either of the locking surfaces is to provide a locking mechanism such that base 50 will not be loosed during or after its application or fastening onto head 30. Base 50 may also include a distal face surface 56. Distal face surface 56 is complementary to proximal face surface 36 on end cap 34. Distal face surface 36 may also include an edge which intersects with the edge on end cap 34 to form shearing or cutting surfaces the two edges can be utilized to cut suture threads placed there between. Other designs may be substituted in order to form a cutting edge between base 50 and head 30.

FIG. 2 illustrates lock head 30 with detachably coupled, elongated, stem 62 attached at the head's proximal end. Stem 62 includes a proximal region 64 having multiple ridges or steps defining a peripheral lock face 66 thereat. The steps or ridges may also be teeth which are utilized in connection with the suture lock applicator.

FIG. 3 diagrammatically illustrates lock base 50 partially fastened to head 30. Prior to base 50 being fastened onto head 30, base 50 travels over stem 62 in the direction indicated by arrow 84 (See base 50' illustrated with dashed lines).

FIG. 4 illustrates a suture lock applicator 60 with a suture lock loaded in the applicator or rivet gun. To the right of the CX1–CX2 line, applicator 60 is shown in cross-section. To the left of line CX1–CX2, applicator 60 is shown diagrammatically. FIG. 4 does not show actual wall or structural thicknesses. The gaps shown in the drawing are not present in applicator gun 60 since the pieces inter-fit over each other.

Suture lock applicator or rivet gun 60 includes an elongated applicator tube 80 with a distal end 72, and includes an optional inner sleeve 70 with a proximal end region 74. Inner sleeve 70 defines a passage through which passes stem 62. The distal end 72 of applicator tube 80 is adapted to abut the proximal end 58 of base 50. In FIG. 4, distal end 72 of applicator tube 80 is shown abutting proximal end 58 of base 50. The proximal end region 74 of inner sleeve 70 has multiple ridges or steps defining a lock face 76 thereat. These steps or ridges may also be teeth which are designed to work in conjunction with the peripheral lock face 66 of stem 62 such that stem 62 is prevented from moving in direction 84 with respect to inner sleeve 70.

Suture lock applicator or rivet gun 60 includes a stationary handle member 96 which is attached to applicator tube 80 and movably coupled to inner sleeve 70. A movable handle member 86 is movably coupled to applicator tube 80. Movable hand member 86 may also be movably coupled to stationary handle 96. The size and shape of movable handle 86 and stationary handle 96 may differ from the illustrated embodiment in FIG. 4. In FIG. 4, movable handle member 86 interfaces with inner sleeve 70 such that movement of movable handle member 86 in the direction of arrow 92 causes longitudinal, proximal movement of inner sleeve 70 (see arrow 82) with respect to applicator tube 80. In the illustrated embodiment, actuator tooth or pin 88 on movable handle member 86 cooperates with the multiple teeth 78 on inner sleeve 70 such that movement of moveable handle member 86 causes the actuator tooth 88 to engage multiple teeth 78, causing proximal longitudinal movement of inner sleeve 70 with respect to applicator tube 80. The tooth 88 on movable member 86 may be different from that illustrated in FIG. 4. The number of teeth 78 on inner sleeve 70 may be increased as necessary to achieve the desired degree of longitudinal movement of inner sleeve 70 and stem 62 relative to applicator tube 80. Movable handle 86 may be biased with respect to applicator tube 80 or stationary handle member 96 through the use of a spring or biasing member 90. The following is an exemplary dimension table of the aforementioned components:

Exemplary Dimension Table

| | |
|---|---|
| Outside diameter of lock base | 0.14 inches |
| Axial length of lock base | 0.24 inches |
| Total axial length of lock base and lock head | 0.28 inches |
| V-channel or cut-out length | 0.04 inches |
| V-channel or cut-out span | 0.03 inches |
| Elongated stem member (short) | 0.9 inches |
| (long) | 4.0 inches |
| Typical number of ridges at proximal region of stem | 6 |
| Typical number of locking ridges at proximal end of lock head | 5 |
| Typical number of locking ridges or lock faces on lock base | 2 |
| Ratio of lock ridges on lock head vs. lock faces on lock base | 3 to 1 |

Figure 5A:
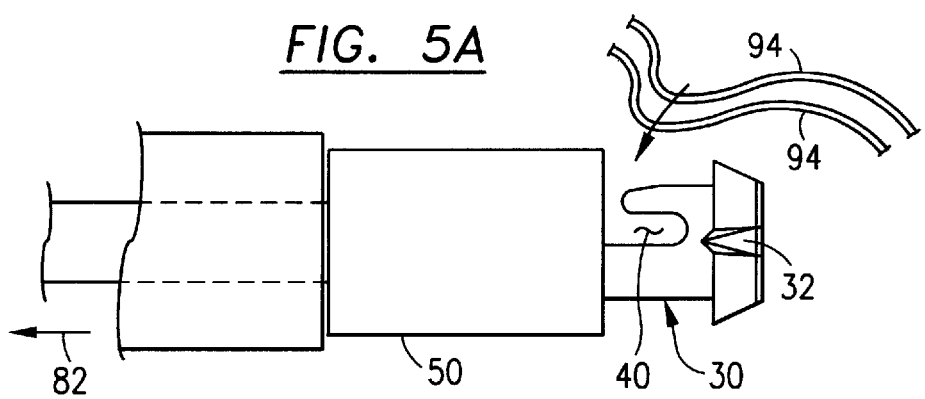
FIGS. 5A, 5B, 5C and 5D illustrate the use of the suture lock or suture lock rivet to capture and lock suture threads.

Operation of suture lock applicator or rivet gun 60 is as follows. The device is designed to be used during one procedure. However, a multiple-use device may also be constructed requiring sterilization between procedures. After the suture threads have been put in place or embedded at the target surgical site (not shown), the distal end of suture lock applicator gun 60 with a lock head 30, and lock base 50 are inserted into a 5 mm trocar or cannula (for example). Suture lock applicator or rivet gun 60 is manipulated to grab both sides of a single suture thread or the proximal ends of two or more suture threads 94 imbedded into tissue at the surgical site. See FIG. 5A. The suture threads 94 are captured in head 30 by placing the extending ends of the threads within cavity 40. Next, in cooperation with stationary handle member 96, movable handle member 86 is moved in direction 92. Such movement causes actuator tooth 88 to engage teeth 78 on inner sleeve 70, which, in turn, causes proximal, longitudinal movement of inner sleeve 70 with respect to applicator tube 80. Because stem 62 is prevented from moving distally in direction 84 with respect to inner sleeve 70 (due to the interface between lock face 76 of inner sleeve 70 and peripheral lock face 66 of stem 62), stem 62 and connected lock head 30 move together with inner sleeve 70 in a proximal direction 82. Biasing member 90 provides an assisting force to cause movable handle member 86 to move in the direction 92. Alternatively, movable handle member 86 can be mounted proximal of stationary handle member 96, such that squeezing the movable handle member and stationary handle member together causes proximal, longitudinal movement of inner sleeve 70 with respect to stationary, applicator tube 80. In this alternative embodiment, biasing member 90 is also mounted proximal of movable handle member 86 such that upon release of movable handle member 86, biasing member 90 causes movable handle member 86 to reset or move proximally.

Figure 5B:
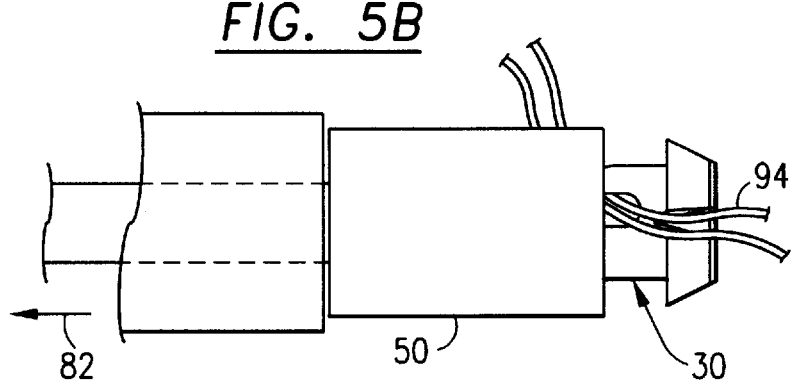

Movable handle member 86 continues to be moved in direction 92 and then in direction 92', causing a ratchet action between actuator tooth 88 and teeth 78. The continued proximal, longitudinal movement of stem 62 and attached lock head 30 causes the proximal end of lock head 30 to enter into the passage defined by lock base 50. Lock base 50 is held stationary with respect to the proximal movement of lock head 30 because the proximal face 58 of lock base 50 abuts applicator tube 80. Through this ratcheting action, the first lock face of lock head 30 and the second lock face of lock base 50 engage such that lock base 50 is locked onto lock head 30. At the same time that lock head 30 is being drawn into lock base 50, lock base 50 is covering suture thread 94 captured within cavity 40 of lock head 30. See FIG. 5B.

Figure 5C:
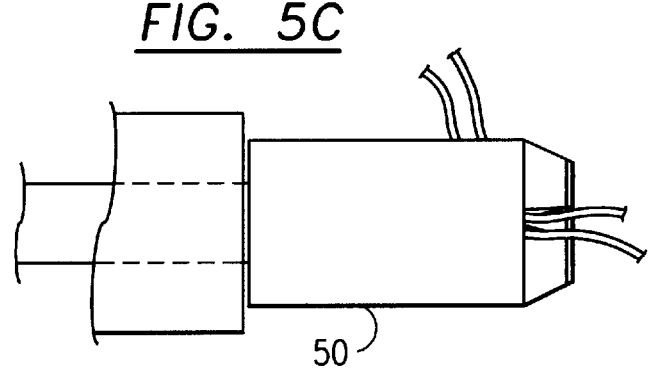
Figure 5D:
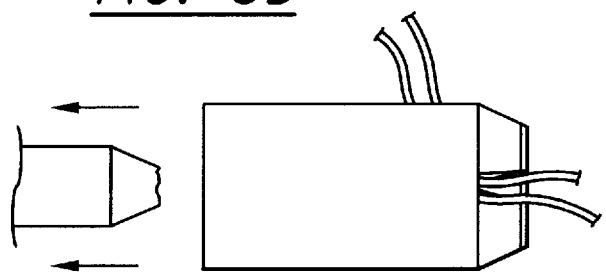

As the distal end face 56 of lock base 50 approaches complementary, proximally facing surface 36 on end cap 34, suture thread 94 becomes trapped within cavity 40 and cut-out 32. See FIG. 5C. As the aforementioned movement of lock head 30 with respect to lock base 50 progresses, the cutting edge of end cap 36 on head 30 and corresponding distal edge 56 of base 50 move closer together trapping suture threads 94 therebetween. As the two edges intersect, the trapped suture threads 94 are cut or severed. See FIG. 7 (distal end view of suture lock 10). Because of cut-out 32, the distal ends of suture threads 94 are uncut and remain locked or captured within suture lock 10. See FIGS. 5C and 6. Finally, additional pulling force is applied in the direction 82 on stem 62 in order to detach the distal end of stem 62 from head 30. See FIG. 5C. During the detaching of stem 62 from lock head 30, end cap 34 provides the necessary stop to prevent lock base 50 from sliding over lock head 30 or sliding beyond its intended lock position. In another embodiment, end cap 34 is not utilized and instead, complementary lock surfaces 38, 52 are designed such that lock base 50 will not slide distally over lock head 30 beyond a predetermined position. For example lock base 50 may include a proximal segment which defines a passage large enough to accommodate stem 62, but too small to accommodate lock head 30 thereby creating a stop thereat.

In an alternative embodiment, inner sleeve 70 of suture lock applicator 60 is eliminated. Instead, actuator tooth 88 of movable handle member 86 engages the peripheral lock surface of stem 62 directly.

The suture lock 10 illustrated in the drawings and discussed above may be envisaged as a suture lock rivet. The suture lock rivet 10 includes a rivet head 34, illustrated as an end cap, and a rivet stem 33, 62. The rivet stem 33, 62 has a first body part 33 and a second body part 62. The first body part 33 is adjacent the rivet head 34. The second body part is stem 62. The first and second body parts of the rivet stem are separated by the breakaway section 42. The suture lock rivet 10 also includes a cut-out 40 adapted to capture at least one suture therein, and the first body part 33 also defines a first locking surface 38. The suture lock rivet 10 also includes a lock base 50. The rivet lock base 50 has a second locking surface 52 complementary to the first locking surface 38 on the first body part 33 of the rivet stem. The suture lock rivet 10 functions substantially similar to suture lock 10 to capture and trap suture threads, thus locking the suture threads at a surgical site.

A rivet gun 60 is diagrammatically illustrated in FIG. 4 Other rivet guns may be used which (a) grip stem body part 62 and (b) coact with lock base 50 to (c) move the base towards rivet head 34. The first body part 33 and rivet head 34 captures suture thread 94 in cavity 40 (FIGS. 5A through 5D) and ultimately force rivet head 34 and first body part 33 to break away from second body part 62 at break point 42. Various guns or delivery systems can be utilized to create this relative axial movement in directions 82 and 83 (FIG. 1A).

The claims appended hereto are meant to cover modifications and changes within the scope and spirit of the present invention.

What is claimed is:

1. A suture lock for locking at least one suture thread, said lock comprising:

an elongated lock head having a proximal end, a distal end and a longitudinal axis, said lock head defining a cutout adapted to capture said at least one suture thread therein, and said lock head defining a first locking surface thereon;

said lock head having a stem connected via a breakaway section to said proximal end of said lock head;

a lock base defining a longitudinal passage adapted to mate with said elongated lock head, said base defining a second locking surface complementary to said first locking surface; and said first and second locking surfaces adapted to lock said base onto said head such that said at least one suture thread is trapped in said cut-out by said base and said stem is adapted to break away from said lock head at said breakaway section;

said elongated lock head defines an end cap at said distal end and at least a part of said cut-out traverses a part of said end cap, said end cap includes a proximally facing surface adapted to interface with a complementary distally facing surface on said lock base, and said corresponding surfaces on said end cap and said base define respective intersecting edges adapted to cut a suture thread placed therebetween.

2. A suture lock as claimed in claim 1 wherein said cut-out defined on said elongated lock head includes a cavity aligned within said head such that said at least one suture thread extends proximally through said cut-out and into said cavity.

3. A suture lock as claimed in claim 2 wherein said head and said lock base are made of one of a biocompatible material and a tissue absorbable material.

4. A suture lock as claimed in claim 3 wherein said first and second locking surfaces define respective locking ridges adapted to interlock.

5. A suture lock as claimed in claim 1 wherein said cut-out defined on said elongated lock head includes a cavity aligned within said head such that said at least one suture thread extends proximally through said cut-out and into said cavity.

6. A suture lock as claimed in claim 1 wherein said cut-out includes at least a partial longitudinal groove.

7. A suture lock as claimed in claim 1 wherein said lock head and said lock base are made of one of a biocompatible material and a tissue absorbable material.

8. A suture lock as claimed in claim 1 wherein said first and second locking surfaces define respective locking ridges adapted to interlock.

9. A suture lock rivet for locking at least one suture thread, said suture lock rivet comprising:

a rivet having a rivet head on a rivet stem, said stem having a first body part and a second body part separated by a breakaway section;

said first body part being adjacent said rivet head and defining a cut-out adapted to capture said at least one suture thread therein, and said first body part defining a first locking surface thereon;

a lock base defining a longitudinal passage adapted to mate with said rivet stem, said base defining a second locking surface complementary to said first locking surface; and said base adapted to lock onto said rivet stem via said first and second locking surfaces such that said at least one suture thread is trapped in said cut-out and said second body part is adapted to break away from said first body part;

wherein at least a part of said cut-out is defined by said rivet head, said rivet head includes a proximally facing surface adapted to interface with a complementary distally facing surface on said lock base, and said corresponding surfaces on said rivet head and said lock base define respective intersecting edges adapted to cut a suture thread placed therebetween.

10. A suture lock rivet as claimed in claim 9 wherein the trapping of said at least one suture thread in said cut-out is via said base.

11. A suture lock rivet as claimed in claim 10 wherein said break away of said second body part from said first body part is via said breakaway section.

12. A suture lock rivet as claimed in claim 11 wherein said cutout defined on said first body part of said rivet stem includes a cavity aligned within said first body part such that said at least one suture thread extends proximally through said cut-out and into said cavity.

13. A suture lock rivet as claimed in claim 12 wherein said rivet head, rivet stem and said lock base are made of one of a biocompatible material and a tissue absorbable material.

14. A suture lock rivet as claimed in claim 13 wherein said first and second locking surfaces define respective locking ridges adapted to interlock.

15. A suture lock rivet as claimed in claim 9 wherein said break away of said second body part from said first body part is via said breakaway section.

16. A suture lock rivet as claimed in claim 9 wherein said rivet head, rivet stem and said lock base are made of one of a biocompatible material and a tissue absorbable material.

17. A suture lock rivet as claimed in claim 9 wherein said first and second locking surfaces define respective locking ridges adapted to interlock.

18. A suture lock rivet as claimed in claim 9 wherein said cut-out defined on said first body part of said rivet stem includes a cavity aligned within said first body part such that said at least one suture thread extends proximally through said cut-out and into said cavity.

19. A suture lock as claimed in claim 9 wherein said cut-out includes at least a partial longitudinal groove.

20. A system for delivery and application of a suture lock for locking at least one suture thread, the system comprising:

a suture lock having an elongated lock head, said lock head having a proximal end, a distal end and a longitudinal axis, said lock head defining a cut-out adapted to capture said at least one suture thread therein, and said lock head defining a first locking surface thereon;

said lock head having a stem connected via a breakaway section to said proximal end of said lock head and said stem having a proximal segment, said segment having a peripheral lock face;

a lock base having a proximal end face and defining a longitudinal passage adapted to mate with said elongated lock head, said base defining a second locking surface complementary to said first locking surface;

said first and second locking surfaces adapted to lock said base onto said head such that said at least one suture thread is trapped in said cut-out by said base and said stem is adapted to break away from said lock head at said breakaway section;

a suture lock applicator having a stationary handle member and an elongated applicator tube attached thereto, said applicator tube having a distal end face adapted to abut said proximal end face of said lock base;

said lock applicator having a movable handle member movably coupled to said applicator tube such that said movable handle member and said stationary handle member cooperate together, said movable handle member having an actuator tooth cooperating with said peripheral lock face on said proximal segment of said stem such that movement of said movable handle member causes said actuator tooth to engage said peripheral lock face and causes longitudinal movement of said stem with respect to said applicator tube.

21. A system as claimed in claim 20 wherein the engaging of said actuator tooth and said peripheral lock face establishes a movably controlled ratchet interface.

22. A system as claimed in claim 20 wherein said breakaway section is one of a detent coupling, a weak link, a latch and a friction lock.

* * * * *